United States Patent [19]
Suzuki et al.

[11] 3,957,790
[45] May 18, 1976

[54] N-(3,3-DIPHENYLPROPYL)-N'-ARALKYL-SUBSTITUTED PIPERAZINES

[75] Inventors: Tadayuki Suzuki, Koshigaya; Toshiharu Megumi, Misato, both of Japan

[73] Assignee: Tokyo Tanabe Company, Ltd., Japan

[22] Filed: Mar. 6, 1975

[21] Appl. No.: 555,827

[30] Foreign Application Priority Data
Mar. 12, 1974  Japan.............................. 49-27745

[52] U.S. Cl............................ 260/268 BZ; 424/250
[51] Int. Cl.$^2$.............. C07D 295/08; C07D 209/02
[58] Field of Search.............................. 260/268 BZ

[56] References Cited
OTHER PUBLICATIONS
I. Aritomi et al., Chemical Abstracts, Vol. 75, 140789m (1971).

*Primary Examiner*—Alton D. Rollins
*Assistant Examiner*—Jose Tovar
*Attorney, Agent, or Firm*—McGlew and Tuttle

[57] ABSTRACT

N-(3,3-Diphenylpropyl)-N'-aralkyl-substituted piperazines which have a structure in which a hydrogen in the N'-benzene ring has been substituted for by —(OCH$_3$)$_n$ (in which $n$ represents an integer from 0 – 3) were synthesized. These compounds are novel compounds that are not found in literature, and have a coronary blood flow increasing action in considerably lower amounts than do conventional piperazine compounds having similar effects.

9 Claims, No Drawings

N-(3,3-DIPHENYLPROPYL)-N-ARALKYL-SUBSTITUTED PIPERAZINES

This invention relates to novel N-(3,3-diphenylpropyl)-N'-aralykyl-substituted piperazines represented by the general formula:

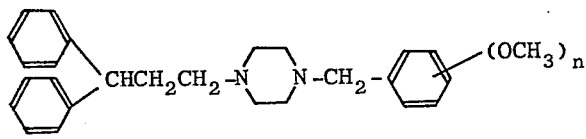 [I]

(in which $n$ represents an integer from 0 – 3) and salts thereof.

Heretofore, a large number of substituted derivatives of piperazine have been known as medicaments, most of which are in use as remedies such as, for example, antihistaminic agents, anti-adrenalinic agents, blood sugar lowering agents, nerve relaxing agents, curatives for cerebral blood vessel disturbances, and coronary blood flow increasing agents, etc. Among the compounds which are of prior knowledge as derivatives of piperazine having the above-mentioned coronary blood flow increasing action are the following:

ethyl-2-(3,4,5-trimethoxycinnamoyl)-4-piperazinyl acetate maleate [Chemical Abstracts, vol. f 36124F (1971)], 1,1-dimethyl-4-phenylpiperazinium iodide [Japanese Circulation Journal, vol. 35, p. 1350 (1971); Folia Pharmacologica Japonica, vol. 67, p. 155 (1971)], N-isopropyl-2-[4-(3,4,5-trimethoxycinnamoyl)-1-piperazinyl] acetamide maleate [Therapie, vol. 29, p. 233 (1974); Annales Pharmaceutiques Francaise, vol. 31, p. 719 (1973)], N-allyl-N-benzhydrylpiperazine dihydrochloride [Farmatsiya (Sofia), vol. 24, p. 8 (1974)], 4-(3,4,5-trimethoxycinnamoyl-1-piperazinylpyrrolidinyl maleate [Farmaco (Sci), vol. 28, p. 131 (1973)], 1-[4,4-di(p-fluorophenyl)butyl]-4-[2,6-dimethylanilinocarbonyl)-methyl]piperazine [Nature (London), vol. 221, p. 184 (1969)], 1-(1,1-difluorophenylmethyl)-4-cinnamylpiperazine [Journal of the American Medical Association, vol. 212, p. 466 (1970)], 1,4-bis-(p-chlorophenylcarbonylethyl)piperazine [Farmatsiya (Sofia), vol. 19, p. 31 (1969)], 1,4-bis-(p-methoxyphenylcarbonylethyl)piperazine [Farmatsiya (Sofia), vol. 19, p. 31 (1969)], 1-benzyl-4-(3,4,5-trimethoxybenzoyl)piperazine [Farmatsiya (Sofia), vol. 19, p. 31 (1969)], 1-(1,5-dimethyl-5-hydroxyhexyl)-4-methylpiperazine [Chemical Abstracts, vol. 74, 22882y (1971)], 1-(1,5-dimethoxy-5-hydroxyhexyl)-4-morpholinocarbonylmethyl-piperazine [Chemical Abstracts, vol. 74, 22882y (1971)], 1-(p-fluorophenylcarbonylpropyl)-4-piperonylpiperazine [Chemical Abstracts, vol. 74, 88056j (1971)], 1-(2-pyrimidyl)-4-piperonylpiperazine [Journal of Medical Chemistry, vol. 11, p. 1151 (1968)], 1-benzhydryl-4-acetonylpiperazine dihydrochloride [French Patent No. 7,009,523; Japanese Early Disclosure of Patent Application No. 46-2931/1971], 3,4-dihydroxy-alpha-[4-(2-methoxyphenyl)-1-piperazinylmethyl]-benzyl alcohol [Arzneimittel Forshung, vol. 19, p. 1698 (1969)].

The above-mentioned prior known derivatives of piperazine, however, have defects in that they are either too weak in the coronary blood flow increasing action [ED$_{50}$(mg)-the dose which can increase the coronary blood flow by 50%] or too strong in toxicity to be put to practical use as remedies for humans. Indeed, only one compound, trimetazidine dihydrochloride, [1-(2,3,4-trimethoxybenzyl)piperazine dihydrochloride)], is now being manufactured as a remedy for humans.

In order to produce medicaments which far surpass the said trimetazidine in coronary blood flow increasing action, the present inventors have carried on an extensive investigation for many years, and as a result, they have succeeded in the preparation of the compounds which are the object of this invention [I].

The compounds which are the object of this invention, [I], are all novel compounds that are not found in literature, and because of their outstanding pharmacological activity, they are usable as medicaments.

To illustrate one of the pharmacological effects of these compounds comparative experiments were carried out on the coronary blood flow increasing action, which was measured in rabbits by the Langendorff method, and on acute toxicity using the said trimetazidine as control, with the results being shown in Table 1. The Langendorff method was carried out according to the method described in Folia Pharmacologica Japonica, vol. 56, p. 1387 (1960), and the acute toxicity was measured by injection into the peritoneal cavities of mice.

From the results shown in Table 1, it can be seen that the compounds which are the object of this invention [I] are, by a factor of ten times or more, superior to trimetazidine in coronary blood flow increasing action; however, their acute toxicity [LD$_{50}$ mg/kg] is 20 – 30%, so that they have a defect in that they possess strong toxicity. Nevertheless, it is very obvious that the compounds of this invention, [I], can exhibit a remedial effect in amounts considerably less than those of trimetazidine.

TABLE 1

Results of comparative experiments on the compounds which are the object of this invention and on trimetazidine for coronary blood flow increasing action [ED$_{50}$ (mg)] and acute toxicity [LD$_{50}$ (mg/kg)]

| Compound tested | ED$_{50}$ (mg) | LD$_{50}$ (mg/kg ip mouse) |
|---|---|---|
| N-(3,3-Diphenylpropyl)-N'-(3,4,5-trimethoxybenzyl)-piperazine dihydrochloride | 0.06 | 89 |
| N-(3,3-Diphenylpropyl)-N'-(3,4-dimethoxybenzyl)-piperazine dihydrochloride | 0.05 | 66 |
| N-(3,3-Diphenylpropyl)-N'-(2,3,4-trimethoxybenzyl)-piperazine dihydrochloride | 0.02 | 100 |
| N-(3,3-Diphenylpropyl)-N'-benzylpiperazine dihydrochloride | 0.08 | 101 |
| Trimetazidine (control compound) | 0.80 | 390 |

The chemical reaction formulas in the process of this invention are as follows.

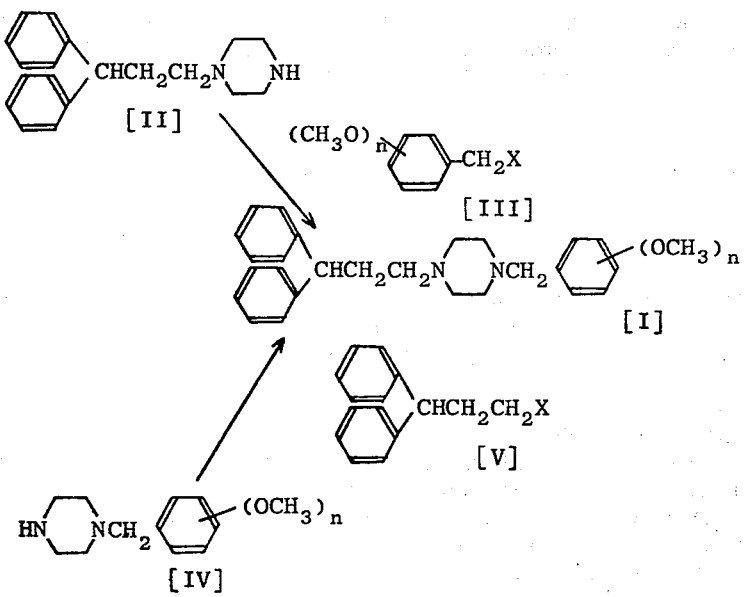

(In the above formulas X and n are the same as described above.)

The compounds which are the object of this invention, [I], can be obtained by subjecting benzyl halogenides or methoxy-substituted benzyl halogenides represented by general formula [III] to a condensation reaction with N-3,3-diphenylpropylpiperazine, [II], in equimolar amounts, or in slight excess thereof. The condensation reaction can be carried out in a solvent at a reaction temperature below 280° and a reaction time of less than 30 hours, but if the reaction is carried out under preferable reaction conditions such that the reaction temperature is 50° – 200°C and the reaction time is 1 – 25 hours, the desired compound may be obtained in high yields of 70% or more. Further, in this condensation reaction, it is also preferable to add a dehydrohalogenating agent such as, for example, tertiary amines (e.g., trimethylamine, triethylamine, tripropylamine, tributylamine, triamylamine, etc.), metal carbonates (e.g., alkali metal carbonates, alkaline earth metal carbonates, heavy metal carbonates, etc.), and the like as the basic condensing agent. That is to say, when this condensation reaction is carried out in the presence of a dehydrohalogenating agent effects can be produced such as lowering of the reaction temperature, shortening of the reaction time, and so on.

As the halogenides represented by general formula [III], chlorides and bromides may be mentioned. As the solvent to be used, examples include alcohols having not more than 12 carbon atoms, halogenated hydrocarbons, hydrocarbons, ketones, esters, ethers, nitrogen-containing compounds, and sulfur-containing compounds, which may be used singly or in the form of an admixture.

The desired compounds, [I], can also be obtained by reacting 3,3-diphenylpropyl halogenides, [V], with N-aralkylpiperazine, [IV], in equimolar amounts, or in slight excess thereof. As said halogenides, [V], chlorides and bromides may again be mentioned. The reaction can be carried out under the same conditions as in the case using the methoxy-substituted benzyl halogenides, [III], described above.

The compounds, [I], obtained in accordance with the process of this invention are mainly oily substances in the free base state. When the occasion demands, for convenience in handling they may be converted into readily crystallized acid addition salts by the use of inorganic or organic acids such as, for example, hydrochloric acid, sulfuric acid, lactic acid, citric acid, malic acid, succinic acid, fumaric acid, etc.

EXAMPLE 1

Preparation of
1-(3,3-diphenylpropyl)-4-benzylpiperazine dihydrochloride:

To a solution containing 17.62 g (0.1 mole) of N-benzyl-piperazine in 100 ml of xylene were added 23.05 g (0.1 mole) of 3,3-diphenylpropyl chloride and 10.1 g (0.1 mole) of triethylamine, and the resulting solution was heated at the refluxing temperature for 2.5 hours. The reaction liquid was left to cool, and the triethylamine hydrochloride which precipitated was filtered out. Then, dry hydrogen chloride gas was passed through this solution, while the solution was cooled so as to precipitate 1-(3,3-diphenyl-propyl)-4-benzylpiperazine dihydrochloride. The crystals were recovered by filtration, and recrystallized from an ethanol and ether mixed solvent to obtain 37.7 g of pure crystals (85.0% yield) with a melting point of 187°–188°C.

Elementary analysis: Calculated as $C_{26}H_{32}N_2Cl_2$ (percent): C, 70.42; H, 7.27; N, 6.32. Found (percent): C, 70.26; H, 7.13; N, 6.48.

EXAMPLE 2

Preparation of
1-(3,3-diphenylpropyl)-4-(3,4-dimethoxybenzyl)piperazine dihydrochloride:

N-3,4-Dimethoxybenzylpiperazine in the amount of 11.8 g (0.05 mole), 11.5 g (0.05 mole) of 3,3-diphenylpropyl chloride, and 5.05 g (0.05 mole) of triethylamine were dissolved in 100 ml of xylene, and the same procedure as that of Example 1 was followed to obtain 18.4 g of 1-(3,3-diphenylpropyl)-4-(3,4-dimethoxybenzyl)piperazine dihydrochloride (73.1% yield) with a melting point of 184°C.

Elementary analysis: Calculated as $C_{28}H_{36}N_2O_2Cl_2$ (percent): C, 66.79; H, 7.21; N, 5.56. Found (percent): C, 66.48; H, 6.90; N, 5.54.

EXAMPLE 3

Preparation of 1-(3,3-diphenylpropyl)-4-(3,4,5-trimethoxybenzyl)-piperazine dihydrochloride:

N-3,3-Diphenylpropylpiperazine in the amount of 14.0 g (0.05 mole), 10.8 g (0.05 mole) of 3,4,5-trimethoxybenzylchloride, and 5.05 g (0.05 mole) of triethylamine were dissolved in 100 ml of xylene, and the same procedure as that of Example 1 was followed to obtain 20.4 g of 1-(3,3-diphenylpropyl)-4-(3,4,5-trimethoxybenzyl)piperazine dihydrochloride (76.7% yield) with a melting point of 178°C.

Elementary analysis Calculated as $C_{29}H_{38}N_2O_3Cl_2$ (percent): C, 65.28; H, 7.18; N, 5.25. Found (percent): C, 65.33; H, 6.98; N, 5.44.

EXAMPLE 4

Preparation of 1-(3,3-diphenylpropyl)-4-(3,4,5-trimethoxybenzyl)-piperazine dihydrochloride:

N-3,3-Diphenylpropylpiperazine in the amount of 2.8 g (0.01 mole) and 2.2 g (0.01 mole) of 3,4,5-trimethoxybenzyl chloride were dissolved in 20 ml of toluene, and heated at the refluxing temperature for 4.5 hours. After the reaction liquid was left to cool, dry hydrogen chloride gas was passed through the reaction liquid while cooling the liquid to precipitate crystals of 1-(3,3-diphenylpropyl)-4-(3,4,5-trimethoxybenzyl)-piperazine dihydrochloride, which were recrystallized from an ethanol and ether mixed solvent to obtain 4.3 g of pure crystals (80.6% yield) with a melting point of 178°C.

Elementary analysis: Calculated as $C_{29}H_{38}N_2O_3Cl_2$ (percent): C, 65.28; H, 7.18; N, 5.25. Found (percent): C, 65.45; H, 7.32; N, 5.25.

EXAMPLE 5

Preparation of 1-(3,3-diphenylpropyl)-4-(2,3,4-trimethoxybenzyl)-piperazine dihydrochloride:

N-2,3,4-Trimethoxybenzylpiperazine in the amount of 13.3 g (0.05 mole), 11.5 g (0.05 mole) of 3,3-diphenylpropyl chloride, 15 ml of dimethylformamide, and 50 ml of toluene were mixed, and the resulting mixture was heated at the refluxing temperature for 4.5 hours. Then, dry hydrogen chloride gas was passed through this reaction liquid while cooling the liquid to precipitate crystals of 1-(3,3-diphenylpropyl)-4-(2,3,4-trimethoxybencyl)-piperazine dihydrochloride, which were recrystallized from isopropyl alcohol to obtain 24.4 g of pure crystals (88.5% yield) with a melting point of 204°–205°C.

Elementary analysis: Calculated as $C_{29}H_{38}N_2O_3Cl_2\cdot H_2O$ (percent): C, 63.15; H, 7.31; N, 5.08. Found (percent): C, 62.85; H, 7.52; N, 5.34.

EXAMPLE 6

Preparation of 1(3,3-diphenylpropyl)-4-(2,3,4-trimethoxybenzyl)-piperazine:

N-3,3-Diphenylpropylpiperazine in the amount of 1.4 g (0.005 mole), 1.1 g (0.005 mole) of 2,3,4-trimethoxybenzyl chloride, and 0.93 g (0.005 mole) of tributylamine were dissolved in 10 ml of ethylene glycol diethyl ether, and the resulting solution was heated at the refluxing temperature for 2.5 hours. The reaction liquid was left to cool, and filtered, and concentration of the filtrate under reduced pressure produced 2.1 g of oily 1-(3,3-diphenylpropyl)-4-(2,3,4-trimethoxybenzyl)piperazine (91.2% yield).

Elementary analysis: Calculated as $C_{29}H_{36}N_2O_3$ (percent): C, 75.62; H, 7.88; N, 6.08. Found (percent): C, 75.55; H, 7.84; N, 6.11.

EXAMPLE 7

Preparation of 1-(3,3-diphenylpropyl)-4-(3,4-dimethoxybenzyl)-piperazine dihydrochloride:

N-3,4-Dimethoxybenzylpiperazine in the amount of 2.36 g (0.01 mole), 2.75 g (0.01 mole) of 3,3-diphenylpropyl bromide, and 1.1 g (0.011 mole) of triethylamine were dissolved in a mixed solvent consisting of 10 ml of pyridine and 10 ml of benzene, and the resulting solution was heated at the refluxing temperature for 1.5 hours. The reaction liquid was filtered after being left to cool, and the filtrate was concentrated under reduced pressure to produce a colorless, transparent, oily substance which was shaken after the addition of ether and water, the ether layer was dried and then, while cooling the liquid, dry hydrogen chloride gas was passed through the liquid to precipitate 1-(3,3-diphenylpropyl)-4-(3,4-dimethoxybenzyl)piperazine dihydrochloride. The crystals of this salt were recrystallized from a methanol and ether mixed solvent to obtain 4.16 g of pure crystals (82.6% yield) with a melting point of 184°C.

Elementary analysis: Calculated as $C_{28}H_{36}N_2O_2Cl_2$ (percent): C, 66.79; H, 7.21; N, 5.56. Found (percent): C, 66.72; H, 7.12; N, 5.51.

EXAMPLE 8

Preparation of 1-(3,3-diphenylpropyl)-4-(3,4,5-trimethoxybenzyl)-piperazine dihydrochloride:

N-3,3-Diphenylpropylpiperazine in the amount of 2.8 g (0.01 mole), 2.61 g (0.01 mole) of 3,4,5-trimethoxybenzyl bromide, and 1.72 g (0.012 mole) of tripropylamine were dissolved in a mixed solvent consisting of 10 ml of acetone and 15 ml of toluene, and the resulting solution was heated at the refluxing temperature for 1 hour. The reaction liquid was filtered after being left to cool, and dry hydrogen chloride gas was passed through the filtrate while cooling said filtrate to precipitate 1-(3,3-diphenylpropyl)-4-(3,4,5-trimethoxybenzyl)piperazine dihydrochloride. The crystals of this salt were recrystallized from a mixed solvent of chloroform and ether to obtain 4.86 g (91.1% yield) of pure crystals with a melting point of 178°C.

Elementary analysis: Calculated as $C_{29}H_{38}N_2O_3Cl_2$ (percent): C, 65.28; H, 7.18; N, 5.25. Found (percent): C, 65.32; H, 7.12; N, 5.30.

EXAMPLE 9

Preparation of 1-(3,3-diphenylpropyl)-4(3,4-dimethoxybenzyl)piperazine dihydrochloride:

N-3,3-Diphenylpropylpiperazine in the amount of 2.8 g (0.01 mole) and 1.87 g (0.01 mole) of 3,4-dimethoxybenzyl chloride were dissolved in 20 ml of methyl ethyl ketone, and the resulting solution was heated at the refluxing temperature for 7.5 hours. After the reaction liquid was left to cool, dry hydrogen chloride gas was passed through the liquid while cooling the liquid to precipitate 1-(3,3-diphenylpropyl)-4-(3,4-dimethoxybenzyl)piperazine dihydrochloride. The crystals of this salt were recrystallized from an ethanol and ether mixed solvent to obtain 4.4 g (87.4% yield) of pure crystals with a melting point of 184°C.

Elementary analysis: Calculated as $C_{28}H_{36}N_2O_2Cl_2$ (percent): C, 66.79; H, 7.21; N, 5.56. Found (percent): C, 66.81; H, 7.23; N, 5.53.

EXAMPLE 10

Preparation of 1-(3,3-diphenylpropyl)-4-(3,4-dimethoxybenzyl)-piperazine dihydrochloride:

N-3,4-dimethoxybenzylpiperazine in the amount of 2.36 g (0.01 mole), 2.3 g (0.01 mole) of 3,3-diphenylpropyl chloride, 2.5 g (0.011 mole) of triamylamine, and 2 ml of quinoline were dissolved in a mixed solvent consisting of 5 ml of cyclohexane and 10 ml of ethyl acetate, and the resulting solution was heated at the refluxing temperature for 2.5 hours. After being left to cool, the reaction liquid was filtered, washed with water, and dried, and then dry hydrogen chloride gas was passed through said liquid, while cooling the liquid, to precipitate 1-(3,3-diphenylpropyl)-4-(3,4-dimethoxybenzyl)piperazine dihydrochloride. The crystals of this salt were recrystallized from a mixed solvent of ethanol and ether to obtain 4.3 g (85.4% yield) of pure crystals with a melting point of 184°C.

Elementary analysis: Calculated as $C_{28}H_{36}N_2O_2Cl_2$ (percent): C, 66.79; H, 7.21; N, 5.56. Found (percent): C, 66.68; H, 7.25; N, 5.62.

EXAMPLE 11

Preparation of 1-(3,3-diphenylpropyl)-4-(3,4,5-trimethoxybenzyl)-piperazine dihydrochloride:

N-3,4,5-Trimethoxybenzylpiperazine in the amount of 2.66 g (0.01 mole), 2.3 g (0.01 mole) of 3,3-diphenylpropyl chloride, 3 ml of dimethylformamide, 1.7 g (0.012 mole) of potassium carbonate, and 0.1 g of sodium iodide were mixed with 20 ml of butyl acetate, and the resulting mixture was heated at the refluxing temperature for 2 hours. The reaction liquid was filtered after being left to cool, and the filtrate was concentrated under reduced pressure to produce an oily residue, which was shaken with ether and water, and the ether layer dried. Then, dry hydrogen chloride gas was passed through the ether solution while cooling said solution to precipitate 1-(3,3-diphenylpropyl)-4-(3,4,5-trimethoxybenyl)piperazine dihydrochloride, whose crystals were recrystallized from a mixed solvent of methanol and ether to obtain 4.76 g (89.2% yield) of pure crystals with a melting point of 178°C.

Elementary analysis: Calculated as $C_{29}H_{38}N_2O_3Cl_2$ (percent): C, 65.28; H, 7.18; N, 5.25. Found (percent): C, 65.19; H, 7.27; N, 5.19.

EXAMPLE 12

Preparation of 1-(3,3-diphenylpropyl)-4-benzylpiperazine dihydrochloride:

N-benzylpiperazine in the amount of 1.76 g (0.01 mole), 2.3 g (0.01 mole) of 3,3-diphenylpropyl chloride, 1.5 g (0.015 mole) of calcium carbonate, and 2 ml of dimethyl sulfoxide were mixed with 20 ml of secondary butanol, and the resulting solution was heated at the refluxing temperature for 2.5 hours. The reaction liquid was filtered after being left to cool, and the filtrate was concentrated under reduced pressure to produce an oily residue, which was shaken with ether and water, and the ether layer dried. Then, dry hydrogen chloride gas was passed through the ether solution while cooling the solution to precipitate 1-(3,3-diphenylpropyl)-4-benzylpiperazine dihydrochloride, whose crystals were recrystallized from methanol to obtaine 3.6 g (81.2% yield) of pure crystals with a melting point of 187°–188°C.

Elementary analysis: Calculated as $C_{26}H_{32}N_2Cl_2$ (percent): C, 70.42; H, 7.27; N, 6.32. Found (percent): C, 70.45; H, 7.31; N, 6.34.

EXAMPLE 13

Preparation of 1-(3,3-diphenylpropyl)-4-(3,4,5-trimethoxybenzyl)-piperazine and organic acid salts thereof:

N-3,3-Diphenylpropylpiperazine in the amount of 2.8 g (0.01 mole), 2.17 g (0.01 mole) of 3,4,5-trimethoxybenzyl chloride, 0.51 g (0.005 mole) of triethylamine, and 1.4 g (0.01 mole) of potassium carbonate were mixed with 20 ml of toluene, and the resulting mixture was heated at the refluxing temperature for 2 hours. The reaction liquid was left to cool, washed by shaking with water, and then the organic liquid layer was concentrated under reduced pressure to obtain 3.8 g (82.5% yield) of oily 1-(3,3-diphenylpropyl)-4-(3,4,5-trimethoxybenzyl)piperazine.

Elementary analysis: Calculated as $C_{29}H_{36}N_2O_3$ (percent): C, 75.62; H, 7.88; N, 6.08. Found (percent): C, 75.33; H, 7.87; N, 6.10.

The above-mentioned oily substance in the amount of 0.5 g (0.0011 mole) was dissolved in 10 ml of ether, to which was added a solution containing 0.5 g (0.0024 mole) of citric acid monohydrate in a methanol - ether mixture from which was produced 0.94 g (97.0% yield) of 1-(3,3-diphenylpropyl)-4-(3,4,5-trimethoxybenzyl)-piperazine dicitrate dihydrate with a melting point of 98°C.

Elementary analysis: Calculated as $C_{41}H_{52}N_2O_{17}.2H_2O$ (percent): C, 55.90; H, 6.41; N, 3.18. Found (percent): C, 55.65; H, 6.22; N, 2.89.

To a methanol solution of 0.5 g (0.0011 mole) of the abovementioned oily substance was added a methanol solution of 1.29 g (0.0025 mole) of fumaric acid, and the resulting solution was concentrated and left to cool to obtain 0.74 g (94.9% yield) of 1; -(3,3-diphenylpropyl)-4-(3,4,5-trimethoxybenzyl)piperazine difumarate monohydrate with a melting point of 194°–195°C.

Elementary analysis: Calculated as $C_{37}H_{44}N_2O_{11}\cdot H_2O$ (percent): C, 62.52; H, 6.52; N, 3.94. Found (percent): C, 62.35; H, 6.40; N, 3.98.

EXAMPLE 14

Preparation of organic acid salts of 1-(3,3-diphenylpropyl)-4-(2,3,4-trimethoxybenzyl)-piperazine:

The amount of 6 g (0.011 mole) of 1-(3,3-diphenylpropyl)-4-(2,3,4-trimethoxybenzyl)piperazine dihydrochloride was dissolved in 50 ml of water, and 20 ml of a 10% sodium hydroxide solution was added. Then, the resulting solution was extracted three times, each time with 20 ml of ether, the ether layers combined, washed with water, and concentrated to a total volume of 10 ml. By adding a methanol-ether solution of 2.7 g (0.013 mole) of citric acid monohydrate to 5 ml of this concentrated solution, 4.4 g (92.7% yield) of 1-(3,3-diphenylpropyl)-4-(2,3,4-trimethoxybenzyl)piperazine dicitrate monohydrate with a melting point of 86°-92°C was obtained.

Elementary analysis Calculated as $C_{41}H_{52}N_2O_{17}\cdot H_2O$ (percent): C, 57.07; H, 6.31; N, 3.25. Found (percent): C, 57.29; H, 6.31; N, 3.52.

By adding a methanol-ether solution of 1.75 g (0.015 mole) of fumaric acid to 5 ml of the concentrated ether solution described above 3.6 g (92.1% yield) of 1-(3,3-diphenylpropyl)-4-(2,3,4-trimethoxybenzyl)piperazine difumarate monohydrate with a melting point of 196°-197°C was obtained.

Elementary analysis Calculated as $C_{37}H_{44}N_2O_{11}\cdot H_3O$ (percent): C, 62.52; H, 6.52; N, 3.94. Found (percent): C, 62.46; H, 6.36; N, 4.22.

EXAMPLE 15

Preparation of 1-(3,3-diphenylpropyl)-4-(3,4-dimethoxybenzyl)-piperazine and organic acid salts thereof:

N-3,3-Diphenylpropylpiperazine in the amount of 2.8 g (0.01 mole), 1.87 g (0.01 mole) of 3,4-dimethoxybenzyl chloride, 0.5 g (0.005 mole) of triethylamine, 1.4 g (0.01 mole) of potassium carbonate, and 2 ml of dimethylformamide were mixed with 20 ml of toluene, and the resulting mixture was heated at the refluxing temperature for 2 hours. The reaction liquid was left to cool, washed by shaking with water, and the organic solvent layer was concentrated under reduced pressure to obtain 3.6 g (83.6% yield) of oily 1-(3,3-diphenylpropyl)-4-(3,4-dimethoxybenzyl)piperazine.

Elementary analysis Calculated as $C_{28}H_{34}N_2O_2$ (percent): C, 78.10; H, 7.96; N, 6.51. Found (percent): C, 78.21; H, 7.99; N, 6.65.

The above-mentioned only substance in the amount of 0.86 g (0.001 mole) was dissolved in methanol and a methanol solution of 0.93 g (0.0044 mole) of citric acid monhydrate added to the solution. The resulting solution was concentrated, left to cool, and 1-(3,3-diphenylpropyl)-4-(3,4-dimethoxybenzyl)piperazine dicitrate precipitated. The crystals were washed with ether to produce 1.52 g (93.3% yield) of pure crystals with a melting point of 98°-104°C.

Elementary analysis: Calculated as $C_{40}H_{50}N_2O_{16}$ (percent): C, 58.96; H, 6.18; N, 3.44. Found (percent): C, 59.24; H, 6.29; N, 3.60.

The above-mentioned oily substance in the amount of 0.86 g (0.002 mole) was dissolved in ether, and by adding thereto a methanol-ether solution of 0.51 g (0.0044 mole) of fumaric acid, 1.25 g (94.3% yield) of 1-(3,3-diphenylpropyl)-4-(3,4-dimethoxybenzyl)piperazine difumarate with a melting point of 214°-215°C was obtained.

Elementary analysis: Calculated as $C_{36}H_{42}N_2O_{10}$ (percent): C, 65.24; H, 6.39; N, 4.23. Found (percent): C, 65.34; H, 6.40; N, 4.08.

EXAMPLE 16

Preparation of 1-(3,3-diphenylpropyl)-4-benzylpiperazine dihydrochloride and difumarate:

N-3,3-Diphenylpropylpiperazine in the amount of 2.8 g (0.01 mole) and 1.3 g (0.01 mole) of benzyl chloride were dissolved in a mixed solvent consisting of 20 ml of toluene and 10 ml of isopropyl alcohol, and the resulting solution was heated at the refluxing temperature for 4.5 hours. The reaction liquid was left to cool, and to it was added ether saturated with hydrogen chloride to precipitate 1-(3,3-diphenylpropyl)-4-benzylpiperazine dihydrochloride. The crystals of this salt were recrystallized from a mixed solvent of ethanol and ether to obtain 3.75 g (84.6% yield) of pure crystals with a melting point of 187°-188°C.

Elementary analysis: Calculated as $C_{26}H_{32}N_2Cl_2$ (percent): C, 70.42; H, 7.27; N, 6.32. Found (percent): C, 70.61; H, 7.32; N, 6.35.

The above-mentioned dihydrochloride in the amount of 2.7 g (0.0061 mole) was dissolved in 10 ml of water, and to this solution was added 20 ml of a 10% sodium hydroxide solution. The resulting solution was extracted three times, each time with 10 ml of ether, the ether layers were combined, washed with water, and dried. By adding a methanol - ether solution of 1.75g(0.015 mole) of fumaric acid to this ether solution, 3.7 g (96.0% yield) of 1-(3,3-diphenyl-propyl)-4-benzylpiperazine difumarate dihydrate with a melting point of 209°-210°C (decomposed) was obtained.

Elementary analysis: Calculated as $C_{34}H_{38}N_2O_8\cdot 2H_2O$ (percent): C, 63.94; H, 6.63, N, 4.39. Found (percent): C, 64.02; H, 6.36, N, 4.34.

What is claimed is:

1. A compound of the formula

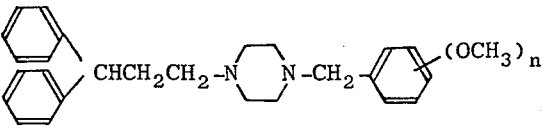

(in which $n$ represents an integer from 0 – 3), or non-toxic acid addition salts thereof.

2. A compound as described in claim 1, in which n is 0 or non toxic acid addition salts thereof.

3. A compound as described in claim 1, in which a methoxy radical is substituted on the 3- and 4-positions of the benzene ring or non-toxic acid addition salts thereof.

4. A compound as described in claim 1, in which a methoxy radical is substituted on the 2-, 3-, and 4-positions of the benzene ring or non-toxic acid addition salts thereof.

5. A compound as described in claim 1, in which a methoxy radical is substituted on the 3-, 4-, and 5-positions of the benzene ring or non-toxic acid addition salts thereof.

6. A compound according to claim 1 which is N-(3,3-Diphenylpropyl)-N'-(3,4,5-trimethoxybenzyl)-piperazine.

7. A compound according to claim 1 which is N-(3,3-Diphenylpropyl)-N'-(3,4-dimethoxybenzyl)-piperazine.

8. A compound according to claim 1 which is N-(3,3-Diphenylpropy)-N'-(2,3,4-trimethoxybenzyl)-piperazine.

9. A compound according to claim 1 which is N-(3,3-Diphenylpropyl)-N'-benzyl piperazine.

* * * * *